US006486306B1

(12) United States Patent
Winge

(10) Patent No.: US 6,486,306 B1
(45) Date of Patent: Nov. 26, 2002

(54) FILTRATION

(75) Inventor: Stefan Winge, Stockholm (SE)

(73) Assignee: Biovitrum AB, Stockholm (SE)

( * ) Notice: Subject to any disclaimer, the term of this patent is extended or adjusted under 35 U.S.C. 154(b) by 866 days.

(21) Appl. No.: 08/750,664

(22) PCT Filed: Jun. 22, 1995

(86) PCT No.: PCT/SE95/00777

§ 371 (c)(1),
(2), (4) Date: Dec. 12, 1996

(87) PCT Pub. No.: WO96/00237

PCT Pub. Date: Jan. 4, 1996

(30) Foreign Application Priority Data

| Jun. 23, 1994 | (SE) | 9402254 |
| Feb. 24, 1995 | (SE) | 9500724 |

(51) Int. Cl.$^7$ .................................................. C07K 1/34
(52) U.S. Cl. ..................... 530/414; 530/412; 435/2; 210/641; 210/651; 210/650; 210/649
(58) Field of Search ................. 530/414, 412; 435/2; 210/641, 651, 650, 649

(56) References Cited

U.S. PATENT DOCUMENTS

| 3,870,801 A | 3/1975 | Tombs |
| 3,874,999 A | 4/1975 | Zaremba et al. |
| 3,919,044 A | 11/1975 | Melnick et al. |
| 4,208,323 A | 6/1980 | Murray et al. |
| 4,473,494 A | 9/1984 | Tye |
| 5,017,292 A | 5/1991 | DiLeo et al. |
| 5,076,933 A | 12/1991 | Glenn et al. |
| 5,221,483 A | * 6/1993 | Glenn et al. ............... 210/641 |

FOREIGN PATENT DOCUMENTS

| AU | B-2140 | 8/1989 |
| EP | 218090 | * 4/1987 |
| EP | 0219295 | 4/1987 |
| EP | 0307373 | 3/1989 |
| WO | WO9426287 | 11/1994 |
| WO | WO 94/26287 | * 11/1994 |

OTHER PUBLICATIONS

Scopes, Protein purification Principles and practice, Springer–Verlag, ISBN 0–387–90726–2, pp. 43–44, 1982.*
Millipore, Catalog 1994–95, pp. 17 and 23, 1994.*
Fraenkel–Conrat, Virology, Prentice–Hall, Inc, Englewood Cliffs, N.J. 07632, 1982.*
Lee et al, *J. Food Science*, (1976) 41:778–786.
Rosenfeld et al, *Biochem Biophy. Res. Commun*, (1972) 47(2):387–392.
Malinowski et al, *Exp. Eye Res.*, (1980) 30:537–543.
Sarfert et al, *J. Basic Microbol*, (1988) 28(1–2):107–117.
Garcia–Gonzalez et al, *Journal Immunological Methods, III*, (1988):17–23.
Palecek et al, *Biotechnol. Prog.*, (1994) 10(2):207–213.
Melling et al, *J. Appl. Chem. Biotechnol.*, (1973) 23:166–167.
Bil'dyukevich et al, *Colloid J. USSR*, (1989) 51(2):349–353 ( English translation).
Iritani et al, *J. Chem Eng. Japan*, 24(2):177–173.
Derwent abstract, WPI Accession No. 94–014376/02 of Soviet Union Patent Publication No. 1,781,355, Dec. 15, 1992.
*Millipore*, Catalog 1994–95, pp. 17 and 23.
Fraenkel–Conrat, *Virology*, Prentice–Hall, Inc., Englewood Cliffs, NJ 17632 (1982).
S. Glasstone, *Textbook of Physical Chemistry*, van Nostrand Co., Toronto, 2nd edition, Fourth Printing, Jul. 1947, pp. 1254–1259.
DiLeo et al, *Nature*, 351 (1991):420–421.
Koenderman et al, *Biotechnology of Blood Proteins*, Rivat et al editors, Colloque INSERM/John Libbey Eurotext Ltd., 227 (1993):81–86.
Michalski et al, *Vox Sang*, 55 (1988):202–210.
Mix, *Developments in Industrial Microbiology*, vol. 15, Proceedings of the 30th General Meeting of the Society for Industrial Microbiology (1974):138–142.
Josic et al, *Journal of Chromatography*, 632 (1993):1–10.
Wallis et al, *Annual Review of Microbiology*, 33 (1980):413–437.
Derwent abstract, WPI Accession No. 94–014376/02 of Soviet Union Patent Publication No. 1,781,355, Dec. 15, 1992.
S. Glasstone,*Textbook of Physical Chemistry*, van Nostrand Co., Toronto, 2nd edition, Fourth Printing, Jul. 1947, pp. 1254–1259.

* cited by examiner

Primary Examiner—Yvonne Eyler
Assistant Examiner—Eliane Lazar-Wesley
(74) Attorney, Agent, or Firm—Fish & Richardson P.C.

(57) ABSTRACT

Filtration methods comprise virus-filtering a solution containing a least one macromolecule. In one embodiment, the total salt content of the solution is within the range of from about 0.2 M to 2 M. In another embodiment, the total salt content of the solution is within the range of from about 0.2 M up to saturation with a salt, and the salt is selected from the group consisting of sodium chloride, potassium chloride, sodium acetate, sodium citrate, sodium phosphate, potassium dyhydrophosphate and combinations thereof. In yet another embodiment, the total salt content of the solution is within the range of from about 0.2 M up to saturation with the salt and the macromolecule is in solution during the virus filtering.

58 Claims, No Drawings

FILTRATION

TECHNICAL FIELD

The present invention relates to a method of virus-filtering a solution that contains at least one macromolecule, by virtue of the total salt content of the solution lying in the range of from about 0.2 M up to saturation of the solution with the salt concerned. The inventive method reduces the residence time and the extent to which the solution need to be diluted, and optimizes the yield when virus-filtering primarily proteins, polysaccharides and polypeptides. The reduction in virus content is at least as good as with conventional techniques where the total salt content is low. The present invention facilitates virus filtration with the aid of the so-called "dead-end" technique, which affords several process and economic advantages in comparison with the tangential virus-filtering technique normally used. When virus-filtering the plasma protein factor IX, the yield obtained in the virus-filtering stage is increased from about 70% to above 95%, by raising the salt content of the solution in accordance with the present invention.

BACKGROUND OF THE INVENTION

The problem of virus contamination of various protein preparations intended for the medication of human beings has received greater notice in recent years. For instance, occasional reports have been submitted concerning, e.g., blood proteins that have been contaminated with hepatitis virus A, hepatitis virus B, hepatitis virus C and/or Human Immunodeficiency Virus (HIV). In keeping with these reports, the authorities of several countries have sharpened their requirements with regard to cleansing protein preparations of their possible virus contamninants.

In present-day, conventional techniques, viruses are inactivated with the aid of chemical additives, primarily solvents and detergents, and/or by exposing the viruses to elevated temperatures. The former method has the drawback of functioning solely on virus with lipid envelopes, for instance hepatitis virus B and HIV. The latter technique mentioned above has the drawback that many proteins are thermally unstable at those temperatures required to effectively reduce the contaminating virus.

U.S. Pat. No. 4,473,494 (assigned to the U.S. Secretary of the Army) discloses a method for production of stroma-free, non-heme protein-free hemoglobin by use of zinc ions to promote precipitation of a zinc ion-bound insoluble hemoglobin complex, followed by membrane ultrafiltration of the zinc-hemoglobin complex from the filtrate fluid medium. In the only step where viruses are said to be removed from hemoglobin, the total salt content is below 0.05 M, i.e. the total content of salt is conventional.

EP-A-0307373 (assigned to Ares-Serono) relates to removal of viruses and/or other contaminants from biological materials in fluid form by using ultrafiltration membranes having a 100,000 Da cut-off. A preferred biological material is human growth hormone. In the examples of EP-A-0307373, the total content of salt in the virus-filtering step lies in the range of from 0.01 up to 0.10 M ($NH_4CO_3$), i.e. the total content of salt is conventional.

There is thus a need for an effective virus-reducing method which can be applied to different types of macromolecules, primarily proteins, and on different types of viruses.

DESCRIPTION OF THE INVENTION

One object of the present invention is to markedly reduce the residence time when virus-filtering solutions that contain macromolecules.

Another object of the present invention is to markedly reduce the liquid volumes when virus-filtering solutions that contain macromolecules.

A further object of the present invention is to reduce the filter area required to effectively virus-filter solutions that contain macromolecules.

Yet another object of the present invention is to achieve a macromolecule yield in excess of about 90% in the virus-filtering stage.

Still another object of the present invention is to reduce the polymerization obtained on the virus filter surface, so as to enable the rate of flow to be increased and the process time to be decreased.

These and other objects are fulfilled by the present invention, which relates to a method of virus-filtering a solution containing at least one macromolecule wherein the total salt content of the solution lies within the range of from about 0.2 M up to saturation of the solution with the salt concerned.

The inventor of this invention has thus found that virus filtration can be effected much more effectively than previously known, by increasing the salt content of the solution. This discovery is surprising, because hitherto in virus filtration of proteins it has been believed that solely the protein concentration, the rate of flow and the pH have had any influence on the process.

It is believed that the enhanced filtering effect achieved at higher salt concentrations is because the protein contracts and can therewith pass more easily through the filter pores. It is also conceivable, that the interaction is reduced between macromolecules themselves and/or between the macromolecules and the material of the filter membrane. It is also conceivable that proteins having a large number of hydrophobic groups are influenced to a greater extent by an elevated salt concentration.

The closer the molecular weight, or relative molecular mass, of the macromolecule lies to the pore size of the filter membrane, the more effective the present invention. The effectiveness of the present invention is also enhanced when the difference in the size and/or the molecular weight of the contaminants and the product increases, i.e. with increasing concentrations of high molecular contaminants in the product.

The present invention also facilitates specific fractions to be separated from a desired product, for instance enables undesirable proteins to be separated from the protein that constitutes the product.

The use of a high salt content according to the present invention, also enables the use of the so-called "dead-end" filtering technique. This preferred embodiment, has several advantages over conventional tangential filtering processes normally applied, especially with a pore size of about 5–30 nm. For instance, the equipment and operating procedures required are much simpler and therewith less expensive. The use of "dead-end" filtration also reduces the loss of the macromolecule, reduces the process time, increases the permeability of the macromolecule through the filter, and also enables a generally constant concentration of the macromolecule to be achieved over the filter as well as a constant membrane pressure. Another advantage with the dead-end filtering technique, is the fact that scaling-up of virus filtering processes from laboratory to industrial scale is considerably facilitated.

When practicing the present invention, the total salt content of the solution suitably lies within the range of from 0.3 up to 3.0 M, preferably within the range of from 0.4 up to 2.5 M, and more preferably within the range of from 0.6 up to 2.0 M. It is particularly preferred that the total salt content of the solution lies within the range of from 0.8 up to When necessary, the total salt content of the solution can be adjusted by adding any acceptable salt. For instance, it is possible to use soluble inorganic salts, soluble organic salts or combinations of such salts. It is assumed that important process advantages are obtained when using salts which exhibit a high salting-out effect in accordance with the so-called Hofmeister series. Reference is here made to S. Glasstone, Textbook of Physical Chemistry, van Nostrand Co., Toronto, 2nd edition, April 1946, pp. 1254–1259. The most important examples of anions which have such high salting-out effect are citrate, tartrate, sulfate, acetate and phosphate. Cations that can be used advantageously when practicing the present invention are monovalent cations, such as sodium, potassium and ammonium, as well as divalent cations, such as calcium. Sodium chloride, potassium chloride, sodium acetate and sodium citrate or combinations thereof are particularly preferred salts in accordance with the invention, in view of the advantages that are afforded by pharmaceutically acceptable additives. It is also conceivable to add one or more salts in sequence, when the filtration process is carried out in two or more steps.

A protein concentration within the range of from about 5 up to about 10 mg/ml solution is often recommended for virus filtration. When applying the present invention, it was surprisingly found that solutions having a higher protein concentration, from about 10 up to about 20 mg/ml, could be processed advantageously through the virus filter.

The solution should have a temperature within the range from 0° C. up to the temperature at which the protein concerned is denatured. The temperature of the solution suitably lies within the range of from 10° C. up to 50° C., preferably from 20° C. up to 35° C.

When practicing the present invention, the solution should have a pH in the range of from about 3 up to about 9, suitably from 4 up to 8. The pH of the protein solution should not lie too close to the isoelectric point of the protein concerned. For instance, in the case of gammaglobulin, a better result is obtained with a pH of 5.5 than with a pH of 6.8.

In the present invention, solution refers to a solution that contains at least 50 percent by weight of water, optionally including one or more solvents, such as methanol, ethanol, acetone or acetonitrile.

The present invention can be used to optimize process procedures when virus-filtering solutions that contain a large number of different types of macromolecules. Examples of such molecules are proteins, polysaccharides and polypeptides or combinations thereof. The origin of the macromolecules is irrelevant to the use of the present invention. The macromolecules may thus derive from the plant kingdom or the animal kingdom or may be produced initially by industrial processes. However, the macromolecules are suitably of human or animal origin or engineered genetically (recombinants).

Particularly appropriate proteins in regard of the present invention are factor VIII, factor IX, antithrombin III, gammaglobulin, albumin, streptokinase, apolipoproteins and growth hormones.

A particularly preferred factor IX product is Nanotiv®, which is supplied by Pharmacia AB, Stockholm, Sweden. The advantage with this product is that its specific activity prior to filtration is sufficiently high to enable the use of a filter of very fine structure. This enables the virus concentration to be lowered to an extremely low level, at the same time as the filtering process itself is very rapid and produces a high yield.

Preferred types of factor VIII are deletion derivatives of recombinant produced factor VIII products. A particularly preferred factor VIII product is r-VIII SQ supplied by Pharmacia AB, Stockholm, Sweden. One advantage with this product is that the recombinant produced product molecule lacks the inactive intermediate part of the natural factor VIII molecule. This gives the molecule a mean molecular weight of about 170,000. A molecule of this size is particularly suited for filtration with such filters as those which enable a considerable virus reduction to be achieved.

Preferred apolipoproteins include apolipoprotein AI (Apo AI), apolipoprotein AII (Apo AII), apolipoprotein AIV (Apo AIV), apolipoprotein E (Apo E) and variants or mixtures thereof. Variants include preforms, fragments and truncated, extended or mutated forms of Apo AI, Apo II, Apo IV and Apo E. Mutated forms in which at least one arginine group has been replaced with a cystein group are particularly preferred. One such mutated form is Apo A-IMilano (Apo A-IM), also produced with recombinant DNA technique by Pharmacia AB, Stockholm, Sweden.

Polysaccharides which are particularly preferred in accordance with the present invention are glycosaminoglycans and bacteria polysaccharides. Examples of glycosarninoglycans are heparins, heparin fragments, heparin derivatives, heparan sulfate and hyaluronic acid. A particularly preferred group of glycosaminoglycans is comprised of low molecular weight heparins having a mean molecular weight of up to about 10,000, preferably from 2,000 up to 8,000.

According to the present invention, particularly suitable polypeptides are bioactive polypeptides, such as recombinant human growth hormones produced in mammalian cells.

The present invention can thus be used to optimize the process of virus-filtering solutions that contain, e.g., proteins, polysaccharides and polypeptides. However, the invention is described in the following with reference to solutions that contain proteins, more specifically proteins that occur naturally in the human organism.

Those viruses that may be present in protein solutions will normally be much larger than the proteins themselves. It is thus presumable that viruses can be removed from proteins in accordance with size, for instance by filtration.

Viruses that can be removed efficiently with the present invention, can have a size smaller than about 350 nm. The size of the viruses that can be removed, suitably is smaller than 200 nm, preferably smaller than 150 nm. Normally, the viruses that can be removed are larger than about 20 nm, i.e. the approximate size of the parvo virus.

The present invention is primarily intended for removing viruses from macromolecules, where the macromolecules are the product of interest. It is, however, within the scope of the invention, to use the present method for separating viruses from macromolecules, where the viruses are the product of interest. An example, is the purification of parvovirus for use as a testing agent, and poliovirus for use a vaccine, wherein e.g. proteins and polysaccharides can be removed by the present method.

Virus filtration is normally carried out in a tangential filtering process or in a so-called "dead-end" filtering process. In tangential virus filtration, the protein solution is pumped around at a constant rate of flow on the retention side, while another pump draws the protein solution through the filter by suction. When a given volume has been obtained on the retention side, a buffer is added on the retention side. This procedure is repeated a number of times, as necessary, with the major part of the remaining protein passing through the filter while retaining the virus on the retention side. Such a process is called diafiltration. The filter is normally discarded after each run, to avoid transferring the virus.

In the case of so-called "dead-end" virus filtration, the same virus filter as that used in tangential virus filtration can be used, although the peripheral equipment and operating procedures are much simpler and less expensive than in the case of tangential virus filtration. Thus, in principle, "dead-end" filtration involves placing the macromolecule-containing solution in a pressure vessel prior to filtration and pressing the solution through the virus filter with the aid of a pressure source, suitably nitrogen (gas).

The degree of fineness of filters generally, is normally given as pore size or the approximate molecular weight (relative molecular mass) at which the molecules are stopped by the filter, the so called cut-off. In the present invention, the virus filters can have a cut-off of about 1,000,000, suitably 500,000. To remove small viruses, the virus filters should have a cut-off of 200,000, preferably 100,000. To reach a maximum virus-reduction, the virus filter should have a cut-off slightly higher than the macromolecule which is virus-filtered.

Virus filters are known in the art and are supplied by Millipore from Massachusetts, USA and Asahi Chemical Industry Co., Ltd. from Japan, among others. Millipore supplies filters having two different types of membrane, depending on the size of the protein concerned. For instance, Millipore supplies, among others, Viresolve™/70 for proteins having a molecular weight, or relative molecular mass, of up to about 70,000, and Vire-solve™/180 for proteins having a molecular weight of up to about 180,000. This latter filter can be used for monoclonal antibodies, for instance. Asahi Chemical Industry supplies, among other things, Planova™ 35 and Planova™ 15 filters, this latter filter being used to remove smaller viruses, such as the polio virus.

As mentioned before, the choice of filter will depend on the size of the protein concerned, among other things. Factor IX, antithrombin m, human serum albumin (HSA) and Apo A-IM (the dimer) all have a molecular weight of roughly 60,000–70,000, wherein Viresolve™/70, for instance, is a suitable alternative. Gammaglobulin has a molecular weight of about 180,000, wherein Viresolve™/180, for instance, is a suitable alternative. The latter filter is also suitable for use with the recombinant produced factor VIII product, r-VIII SQ, which has a molecular weight of about 170,000, as mentioned before.

The possibility of choosing a fine structure filter also assumes that the protein solution has a high degree of purity prior to filtration. In turn, the use of a fine structure filter is a prerequisite for the ability to produce protein solutions which have a very low virus content in the end product. Thus, in order to be able to reduce the virus concentration to a very low level, there is required a filter of very fine structure, for instance Viresolve™/70. The virus concentration cannot be lowered to quite such a low level when using Viresolve™/180.

The effectiveness, or efficiency, of the filtering stage is influenced by the purity of the protein solution delivered to the filter. In this regard, a high specific activity prior to filtration results in a higher yield in the filtering stage. For instance, in the case of preferred embodiments applied when filtering solutions that contain factor DC, it has been found that the protein yield in the filtering stage can be increased from about 70% to above 95%. However, when practicing the present invention, it is possible to achieve protein yields of above 90%, even when working with solutions of low specific activity.

With the present invention, it is possible to reduce the content of very small non-enveloped viruses, such as the parvovirus, by at least 3 logs, suitably at least 4 logs, and preferably at least 5 logs. The reduction is very good with the tangential technique, but even better with the "dead-end" technique, when applied according to the present invention.

According to the invention, virus filtration is preferably carried out at the end of a protein manufacturing sequence, since a high specific activity prior to filtration will result in a higher protein yield in the filtering stage. The present invention is preferably applied as a last purification stage, optionally followed by a stage for adjusting, for instance, protein concentration, salt content or the pH of the end product. A following diafiltration stage using a UF-membrane may also be applied to remove salts which although advantageous from a process or economic aspect during virus filtration should not be included in the end product. Protein solutions which are ready for administration will normally contain a physiological solution, for instance 0.15 M sodium chloride at a pH of 7, in combination with one or more stabilizers, such as saccharose or amino acids. The virus filtration process may also be carried out in two or more steps, with or without intermediate process steps.

The present invention effectively reduces the content of virus with lipid envelopes and viruses without lipid envelopes. Examples of viruses without a lipid envelope are the hepatitis virus A, polio virus and parvo virus, which are relatively small viruses. Examples of viruses with a lipid envelope are the hepatitis virus B, the hepatitis virus C and the Human Immunodeficiency Virus (HIV).

The invention will now be illustrated in more detail with the aid of exemplifying, non-limiting examples.

EXPERIMENTAL SECTION

Experiments were carried out in which the sieving coefficient of proteins, or protein permeability factor, was first determined at different filtrate flowrates. The sieving coefficient, or protein permeability factor, is given as P/R, where P is the concentration of protein on the permeate side (the filtrate side) measured by absorption at 280 nm ($A_{280}$) and R is the concentration of protein on the retention side (R) measured by absorption at 280 nm ($A_{280}$). The filtrate flowrate which gave the highest sieving coefficient in the absence of polymerization on the filter was then chosen. A yield optimization was also made with some macromolecules.

EXAMPLE 1

Experiments were carried out with factor IX as the macromolecule, to illustrate the effect of two salt contents on the protein sieving characteristic, the diafiltration volume and the yield. A commercial solution containing factor IX, Nanotiv®, was supplied by Pharmacia AB, Stockholm, Sweden. The solution containing factor IX was obtained from human blood plasma and prior to filtration had been treated in a sequence involving anion exchange, chemical virus inactivation, affinity chromatography and cation exchange. The solution was ultra-filtered between each stage, except between the chemical virus inactivating stage and the affinity chromatographic stage.

Experimental Conditions

Degree of purity of the entering protein solution: high.
Buffer: 0.144 M NaCl+0.0055 M sodium citrate.
Total salt content: about 0.15 M.
Protein concentration: 0.5–1.0 $A_{280}$ units.
Protein solution pH: 7.
Experimental temperature: room temperature (about 23° C.).
Virus separating filters: Viresolve™/70.
Filtering technique: tangential.
Filter area: ⅓ ft²
Retention flowrate: 41 l/h.
Pump: Watson-Marlow 504.
Transmembrane pressure: 0.2–0.3 bar.

TABLE 1

Determining the protein sieving coefficient.

| Experiment | Filtrate flowrate, ml/min | P/R, % |
|---|---|---|
| 1 | 3.5 | 35.0 |
| 2 | 6.9 | 39.6 |
| 3 | 10.7 | 45.8 |
| 4 | 14.1 | 56.2 |
| 5 | 17.6 | 55.6 |
| 6 | 20.8 | 58.3 |
| 7 | 24.3 | 61.7 |

An optimal filtrate flowrate of 20.8 ml/min was obtained by determining the protein sieving coefficient.

TABLE 2

Yield optimization. Filtrate flowrate: 20.8 ml/min. High degree of protein solution purity. Buffer: 0.144 M NaCl + 0.0055 M sodium citrate. Total salt content: about 0.15 M.

| Experiment | Filtration time | P/R, % |
|---|---|---|
| 1 | 3 min 10 s | 55.1 |
| 2 | 6 min 25 s | 52.1 |
| 3 | 10 min 40 s | 44.5 |
| 4 | 13 min 20 s | 34.0 |

Diafiltration with a dilution of about 1 volume unit per volume unit of entering protein solution (1+1) resulted in a yield of about 90%.

EXAMPLE 2

The same conditions were applied as those applied in Example 1, with the exception that in this case the buffer comprised 1.0 M NaCl+0.01 M sodium citrate, which gave a total salt content of about 1.0 M.

TABLE 3

Determining the protein sieving coefficient.

| Experiment | Filtrate flowrate, ml/min | P/R, % |
|---|---|---|
| 1 | 3.5 | 55.2 |
| 2 | 6.9 | 55.7 |
| 3 | 10.7 | 61.4 |
| 4 | 14.1 | 68.4 |
| 5 | 17.6 | 74.2 |
| 6 | 20.8 | 77.0 |
| 7 | 24.3 | 80.5 |

This determination of the protein sieving coefficient gave an optimal filtrate flowrate of 24.3 ml/min.

TABLE 4

Yield optimization. Filtrate flowrate: 24.3 ml/min.

| Experiment | Filtration tim | P/R, % |
|---|---|---|
| 1 | 2 min 30 s | 72 |
| 2 | — | 68 |
| 3 | 7 min 14 s | 65 |
| 4 | 9 min 38 s | 55 |

Diafiltration with a dilution of about 0.3 volume units per volume unit of entering solution (1+0.3) resulted in a yield of >95%.

EXAMPLE 3

The virus removing effect achieved with the experiments disclosed in Examples 1 and 2 was determined by a virus study. The study was carried out on parvovirus, which are non-lipid-enveloped viruses and which have a size of 20–25 nm. In principle, experiments with such viruses fall into the "worst case" category since they are some of the smallest viruses known.

The parvovirus was added to the solutions containing factor IX, with a salt content of 0.144 M NaCl+0.0055 M sodium citrate (experiment 1) and 1.0 M NaCl+0.01 M sodium citrate (experiment 2) respectively. The solutions were then virus-filtered in accordance with Examples 1 and 2. The solutions were analyzed with respect to the parvovirus both before and after virus filtration.

| Experiment | Virus reduction |
|---|---|
| 1 | $1 \times 10^{3.7}$ |
| 2 | $1 \times 10^{4.0}$ |

The results show that virus filtration in accordance with Examples 1 and 2 fulfil the requirements placed by the authorities on the virus reduction in one process step. Furthermore, the use of a high salt content in accordance with the invention is at least equally as effective in removing virus as previously known techniques.

EXAMPLE 4

The same conditions were applied as those applied in Example 1, with the exception that the entering protein solution was not as pure.

Diafiltration with dilution of about 3 volume units per volume unit of entering protein solution (1+3) resulted in a yield of about 65%.

EXAMPLE 5

The same conditions were applied as those applied in Example 2, with the exception that the entering protein solution was not as pure.

Diafiltration with dilution of about 3 volume units per volume unit of entering protein solution (1+3) resulted in a yield of 89%. The yield of factor IX:C was 87%.

EXAMPLE 6

Experiments were carried out with factor IX as the macromolecule, to show the effect of four salt contents on the protein sieving coefficient, the diafiltration volume and the yield, with other experiment conditions being constant. The Nanotiv® solution used was similar to that used in Example 1. The experimental conditions applied were the same as those applied in Example 1.

TABLE 5

Determining the protein sieving coefficient. The buffer comprised 0.144 M NaCl + 0.0055 M sodium citrate. Total salt content: about 0.15 M.

| Experiment | Filtrate flowrate, ml/min | P/R, % |
|---|---|---|
| 1 | 3.5 | 25 |
| 2 | 6.9 | 28 |
| 3 | 14.1 | 43 |
| 4 | 20.8 | 49 |
| 5 | 24.3 | 50 |

TABLE 6

Determining the protein sieving coefficient. The buffer comprised 0.5 M NaCl + 0.01 M sodium citrate. Total salt content: about 0.5 M.

| Experiment | Filtrate flowrate, ml/min | P/R, % |
|---|---|---|
| 1 | 3.5 | 36 |
| 2 | 6.9 | 44 |
| 3 | 14.1 | 61 |
| 4 | 20.8 | 67 |
| 5 | 24.3 | 69 |

TABLE 7

Determining the protein sieving coefficient. The buffer comprised 1.0 M NaCl + 0.01 M sodium citrate. Total salt content: about 1.0 M.

| Experiment | Filtrate flowrate, ml/min | P/R, % |
|---|---|---|
| 1 | 3.5 | 49 |
| 2 | 6.9 | 60 |
| 3 | 14.1 | 72 |
| 4 | 20.8 | 74 |
| 5 | 24.3 | 76 |

TABLE 8

Determining the protein sieving coefficient. The buffer comprised 1.5 M NaCl + 0.01 M sodium citrate. Total salt content: about 1.5 M.

| Experiment | Filtrate flowrate, ml/min | P/R, % |
|---|---|---|
| 1 | 3.5 | 48 |
| 2 | 6.9 | 56 |
| 3 | 14.1 | 73 |
| 4 | 20.8 | 76 |
| 5 | 24.3 | 74 |

It is evident from Tables 5 to 8 that the present invention provides a marked improvement in the process conditions when virus-filtering factor IX, solutions in comparison with previously known techniques where low salt contents have been used.

EXAMPLE 7

Experiments were carried out with factor IX as the macromolecule to show the effect of three different salts on the protein sieving coefficient, the diafiltration volume and the yield, with other experiment conditions being constant. The Nanotiv® solution used was similar to that used in Example 1. The conditions applied were the same as those applied in Example 1.

TABLE 9

Determining the protein sieving coefficient. The buffer comprised 0.5 M potassium dihydrophosphate. Total salt content: 0.5 M.

| Experiment | Filtrate flowrate, ml/min | P/R, % |
|---|---|---|
| 1 | 3.5 | 34 |
| 2 | 6.9 | 48 |
| 3 | 14.1 | 57 |
| 4 | 20.8 | 55 |

TABLE 10

Determining the protein sieving coefficient. The buffer comprised 0.5 M NaCl. Total salt content: 0.5 M.

| Experiment | Filtrate flowrate, ml/min | P/R, % |
|---|---|---|
| 1 | 3.5 | 27 |
| 2 | 6.9 | 43 |
| 3 | 14.1 | 50 |
| 4 | 20.8 | 46 |

TABLE 11

Determining the protein sieving coefficient. The buffer comprised 0.5 M barium chloride. Total salt content: 0.5 M.

| Experiment | Filtrate flowrate, ml/min | P/R, % |
|---|---|---|
| 1 | 3.5 | 24 |
| 2 | 6.9 | 36 |
| 3 | 14.1 | 34 |
| 4 | 20.8 | — |

It will be evident from Tables 9 to 11 that the present invention can be carried out advantageously with a number of different salts. It will also be seen that the protein sieving coefficient increases when using salts that have a high salting-out effect in accordance with the Hofmeister series (potassium dihydrophosphate) in comparison with a salt that has a low salting-out effect (barium chloride).

EXAMPLE 8

Experiments were carried out with gammaglobulin as the macromolecule to show the effect of salt content on protein sieving coefficient, diafiltration volume and yield. The solution containing gammaglobulin was a commercial product obtained from blood plasma, Gammonativ®, supplied by Pharmacia AB, Stockholm, Sweden. Prior to the gamma-globulin solution had been purified by an intitial Cohn fractionation by a chromatographic stage.

The experimental conditions applied were the same as those applied in Example 1, with the exception that the virus-removing filter was a Viresolve™/180 filter, the pH of the solution was 6.8 and the protein concentration was 2.5–5.0 $A_{280}$ units. The buffer comprised 2.2% albumin+ 0.15 M NaCl+0.02 M NaAc+0.075 M glycine. Total salt content: 0.17 M.

TABLE 12

Determining the protein sieving coefficient.

| Experiment | Filtrate flowrate, ml/min | P/R, % |
|---|---|---|
| 1 | 3.5 | 32 |
| 2 | 6.9 | 35 |
| 3 | 10.7 | 41 |
| 4 | 14.1 | 51 |
| 5 | 17.6 | 59 |
| 6 | 20.8 | 63 |
| 7 | 24.3 | 69 |

Determination of the protein sieving coefficient gave an optimal filtrate flowrate of 20.8 ml/min.

EXAMPLE 9

The same conditions were applied as those applied in Example 8, with the exception that in this case the buffer comprised 2.2% albumin+1.0 M NaCl+0.02 M NaAc+0.075 M glycine. Total salt content: about 1.0 M.

TABLE 13

Determining the protein sieving coefficient.

| Experiment | Filtrate flowrate, ml/min | P/R, % |
|---|---|---|
| 1 | 3.5 | 38 |
| 2 | 6.9 | 57 |
| 3 | 10.7 | 64 |
| 4 | 14.1 | 71 |
| 5 | 17.6 | 75 |
| 6 | 20.8 | 80 |
| 7 | 24.3 | 81 |

Determination of the protein sieving coefficient gave an optimal filtrate flowrate of 20.8 ml/min.

Optimization of the yield at a filtrate flowrate of 20.8 ml/min. and a residence time of up to 10 min gave a P/R quotient of between 60% and 68%.

Diafiltration with a dilution degree of about 1 volume unit per volume unit of entering protein solution (1+1) resulted in a yield of 90%.

EXAMPLE 10

The same conditions were applied as those applied in Example 8, with the exception that in this case the pH of the solution was 5.5.

TABLE 14

Determining the protein sieving coefficient.

| Experiment | Filtrate flowrate, ml/min | P/R, % |
|---|---|---|
| 1 | 3.5 | 41 |
| 2 | 6.9 | 47 |
| 3 | 14.1 | 62 |
| 4 | 20.8 | 72 |
| 5 | 24.3 | 74 |

EXAMPLE 11

The same conditions were applied as those applied in Example 10, with the exception that in this case the buffer comprised 2.2% albumin+1.0 M NaCl+0.02 M NaAc+0.075 M glycine. Total salt content: about 1.0 M.

TABLE 15

Determining the protein sieving coefficient.

| Experiment | Filtrate flowrate, ml/min | P/R, % |
|---|---|---|
| 1 | 3.5 | 57 |
| 2 | 6.9 | 67 |
| 3 | 14.1 | 78 |
| 4 | 20.8 | 88 |
| 5 | 28.1 | 90 |

EXAMPLE 12

Experiments were carried out with albumin as the macromolecule to show the effect of salt content on protein sieving coefficient, diafiltration volume and yield. The 4% solution containing Human Serum Albumin (HSA) obtained from blood plasma was supplied by Pharmacia AB, Stockholm, Sweden. Prior to filtration, the albumin-containing solution had been purified by combined Cohn fractionation and a chromatographic stage.

The experimental conditions applied were the same as those applied in Example 1, with the exception that the protein concentration was about 10 $A_{280}$ units. The buffer comprised 0.15 M NaCl+0.02 M NaAc, resulting in a total salt content of 0.17 M.

TABLE 16

Determining the protein sieving coefficient.

| Experiment | Filtrate flowrate, ml/min | P/R, % |
|---|---|---|
| 1 | 3.5 | 34 |
| 2 | 6.9 | 39 |
| 3 | 14.1 | 50 |
| 4 | 20.8 | 51 |
| 5 | 24.3 | 50 |

Determination of the protein sieving coefficient resulted in an optimal filtrate flowrate of 20.8 ml/min.

EXAMPLE 13

The same conditions were applied as those applied in Example 12, with the exception that in this case the buffer comprised 1.0 M NaCl+0.02 M NaAc, resulting in a total salt content of about 1.0 M.

TABLE 17

Determining the protein sieving coefficient.

| Experiment | Filtrate flowrate, ml/min | P/R, % |
|---|---|---|
| 1 | 3.5 | 39 |
| 2 | 6.9 | 57 |
| 3 | 14.1 | 62 |
| 4 | 20.8 | 64 |
| 5 | 24.3 | 60 |

Diafiltration with a dilution degree of about 1 volume unit per volume unit of entering protein solution (1+1) resulted in a yield of 85%.

EXAMPLE 14

Experiments were carried out with factor IX as the macromolecule, to show the effect of the retention flowrate on the protein sieving coefficient with other conditions constant. The commercial Nanotiv® solution used was similar to the solution used in Example 1. The conditions applied were the same as those applied in Example 1, with the exception that in this case the buffer comprised 1 M NaCl+6.4 mM sodium citrate with a pH of 7.0.

TABLE 18

Determining the protein sieving coefficient at different retention flowrates.

| Experiment | Retention flowrate, l/h | Filtrate flowrate, ml/min | P/R % |
|---|---|---|---|
| 1 | 1 | 14 | 79 |
| 2 | 1 | 19 | 85 |
| 3 | 1 | 24 | 85 |
| 4 | 10 | 14 | 72 |
| 5 | 10 | 19 | 76 |
| 6 | 10 | 24 | 76 |
| 7 | 20 | 14 | 62 |
| 8 | 20 | 19 | 70 |
| 9 | 20 | 24 | 76 |
| 10 | 30 | 14 | 65 |
| 11 | 30 | 19 | 69 |
| 12 | 30 | 24 | 73 |
| 13 | 40 | 14 | 60 |
| 14 | 40 | 19 | 64 |
| 15 | 40 | 24 | 70 |
| 16 | 50 | 14 | 57 |
| 17 | 50 | 19 | 61 |
| 18 | 50 | 24 | 68 |
| 19 | 60 | 14 | 51 |
| 20 | 60 | 19 | 56 |
| 21 | 60 | 24 | 62 |
| 22 | 90 | 14 | 46 |
| 23 | 90 | 19 | 56 |
| 24 | 90 | 24 | 56 |

Lower retention flowrates result in higher protein permeability through the filter.

EXAMPLE 15

Experiments were carried out with factor IX as the macromolecule in a solution having a high salt content, to show the effect of type of virus-filtering technique on dilution, yield, protein sieving coefficient and process time, with other experimental conditions being essentially constant. The experimental conditions applied, including the Nanotiv® solution were the same as those applied in Example 1, with the exception of the following differences:

| Virus filtration technique | Tangential | "Dead-end" |
|---|---|---|
| Amount of protein solution prior to virus filtration (g): | 294 | 1124 |
| Protein conc. ($A_{280}$ units): | 0.66 | 1.0 |
| Retention flowrate (l/h): | 40 | 0 |
| Filtrate flowrate buffer (ml/min): | 24 | 28 |

TABLE 19

Determining dilution, yield, protein sieving coefficient and process time using different virus-filtering techniques.

| Virus filtration technique | Tangential | "Dead-end" |
|---|---|---|
| Amount of protein solution after virus filtration (g): | 459 | 1146 |
| Dilution: | 1 + 0.56 | 1 + 0.02 |
| Yield (%): | 89 | 94 |
| Protein sieving coefficient (P/R in %): | 17–64 | 92–98 |
| Actual filtrate flowrate (ml/min): | 15–24 | 7–25 |
| Process time (kIU factor IX/h): | 31 | 105 |
| Protein load ($A_{280}$ units/ft$^2$): | 413 | 2360 |

Virus filtration of factor IX using the "dead-end" technique means less dilution, shorter process times and results in a higher yield and protein permeability.

EXAMPLE 16

Experiments were carried out with factor IX as the macromolecule, to show the effect of salt content on yield and the protein sieving coefficient when virus-filtering in accordance with the "dead-end" technique, with remaining experimental conditions constant. In addition to NaCl, the buffer also contains 6.4 mM sodium citrate (pH 7.0) in both cases. The conditions applied, including the Nanotiv® solution were the same as those applied in Example 1, with the exception of the following differences:

| | | |
|---|---|---|
| Salt content (M NaCl): | 1.0 | 0.15 |
| Amount of protein solution prior to virus filtration (g): | 293 | 256 |
| Protein conc. ($A_{280}$ units): | 0.84 | 0.84 |
| Retention flowrate (l/h): | 0 | 0 |
| Filtrate flowrate buffer (ml/min): | 28 | 28 |

TABLE 20

Determining dilution, yield and protein sieving coefficient when using a buffer which contained 1.0 M NaCl + 6.4 mM sodium citrate (pH 7.0).

| Amount of filtrate, g | P/R, % | Flowrate, ml/min |
|---|---|---|
| 50 | 83 | 31 |
| 100 | 82 | 28 |
| 150 | 84 | 30 |
| 200 | 81 | 23 |
| 250 | 81 | 21 |

| Sample | Amount, g | Protein conc., $A_{280}$ units | Yield, % |
|---|---|---|---|
| Prior to virus filtration | 293 | 0.84 | 100 |
| Filtrate | 284 | 0.67 | 77 |
| Wash | 30 | 0.47 | 6 |

A total yield of 83% was obtained over the virus filter, with a dilution degree of 1+0.07. Process time 264 kIU factor IX/h.

TABLE 21

Determining dilution, yield, protein sieving coefficient and process time when using a buffer containing 0.15 M NaCl + 6.4 mM sodium citrate (pH 7.0).

| Amount of filtrate, g | P/R, % | Flowrate, ml/min |
|---|---|---|
| 50 | 61 | 22 |
| 100 | 62 | 20 |
| 150 | 63 | 18 |
| 200 | 63 | 16 |

| Sample | Amount, g | Protein conc., $A_{280}$ units | Yield, % |
|---|---|---|---|
| Prior to virus filtration | 256 | 0.84 | 100 |
| Filtrate | 243 | 0.50 | 56 |
| Wash | 30 | 0.50 | 7 |

A total yield of 63% was obtained with the virus filter, with a dilution degree of 1+0.07. Process time 194 kIU factor IX/h.

EXAMPLE 17

Experiments were carried out with antithrombin (AT III) as the macromolecule in a solution of low salt content, to show the effect of this type of virus filtration technique on dilution, yield, protein sieving coefficient and process time, with other conditions being essentially constant. The commercial ATenativ® solution used was delivered by Pharmacia AB, Stockholm, Sweden. The buffer contained 0.12 M NaCl+1 mM sodium phosphate (pH 7.4) in both cases. The conditions applied were the same as those applied in Example 1, with the exception of the following differences:

| Virus filtration technique | Tangential | "Dead-end" |
|---|---|---|
| Amount of protein solution prior to virus filtration (g): | 967 | 970 |
| Protein conc. ($A_{280}$ units): | 9.1 | 9.1 |
| Retention flowrate (l/h): | 40 | 0 |
| Filtrate flowrate buffer (ml/min): | 24 | 24 |

TABLE 22

Determining dilution, yield, protein sieving coefficient and process time with the aid of different virus filtration techniques

| Virus filtration technique | Tangential | "Dead-end" |
|---|---|---|
| Amount of protein solution after virus filtration (g): | 1692 | 989 |
| Dilution: | 1 + 0.75 | 1 + 0.02 |
| Yield (%): | 97 | 97 |
| Protein sieving coefficient (P/R in %): | 73–86 | 95–98 |
| Actual filtrate flowrate (ml/min): | 15–24 | 8–14 |
| Process time (kIU AT III/h): | 37 | 53 |
| Protein load ($A_{280}$ units/ft$^2$): | 18477 | 18481 |
| Filtration efficiency (l/m$^2$ filter*h): | 9 | 12 |

Virus filtration of AT III when applying the "dead-end" technique means less dilution, affords higher protein permeability and shorter process times.

EXAMPLE 18

Experiments were carried out with antithrombin (AT III) as the macromolecule, to show the effect of salt content on yield and protein permeability (sieving coefficient) when virus-filtering in accordance with the tangential technique, with remaining experimental conditions being constant. In addition to NaCl, the buffer contained 1 mM sodium phosphate (pH 7.4) in all experiments. The conditions applied, including the ATenativ® solution, were the same as those applied in Example 17, with the exception that the retention flowrate was 20 l/h in all experiments.

TABLE 23

Determining the protein sieving coefficient at different salt contents and different filtrate flowrates.

| Experiment | Salt content, M NaCl | Filtrate flowrate ml/min | P/R % |
|---|---|---|---|
| 1 | 0.15 | 14 | 79 |
| 2 | 0.15 | 19 | 84 |
| 3 | 0.15 | 24 | 87 |
| 4 | 1.0 | 14 | 87 |
| 5 | 1.0 | 19 | 90 |
| 6 | 1.0 | 24 | 89 |

High salt content result in improved protein permeability with regard to AT III.

EXAMPLE 19

Experiments were carried out with Human Serum Albumin (HSA) as the macromolecule in a solution having a high salt content, to show the effect of type of virus filtration technique on dilution, yield, protein permeability and process time, with other experimental conditions being essentially constant. The HSA solution used was similar to the solution used in Example 12. The buffer contained 1.0 M NaCl+20 mM sodium acetate (pH=7.4) in all experiments. The conditions applied were the same as those applied in Example 1, with the exception of the following differences:

| Virus filtration technique | Tangential | "Dead-end" |
|---|---|---|
| Amount of protein solution prior to virus filtration (g): | 200 | 6460 |
| Protein conc. ($A_{280}$ units): | 10 | 9.2 |
| Retention flowrate (l/h): | 40 | 0 |
| Filtrate flowrate buffer (ml/min): | 24 | 28 |

TABLE 24

Determining dilution, yield, protein sieving coefficient and process time when using tangential virus filtration.

| Amount of filtrate, g | P/R, % |
|---|---|
| 50 | 39 |
| 100 | 57 |
| 200 | 62 |
| 300 | 64 |
| 350 | 60 |

| Sample | Amount, g | Protein conc., $A_{280}$ units | Yield, % |
|---|---|---|---|

TABLE 24-continued

Determining dilution, yield, protein sieving coefficient and process time when using tangential virus filtration.

| | | | |
|---|---|---|---|
| Prior to virus filtration | 200 | 10.0 | 100 |
| Filtrate | 144 | 7.0 | 51 |
| Wash 1 | 100 | 4.4 | 22 |
| Wash 2 | 100 | 4.2 | 12 |

A total yield of 85% was obtained over the virus filter, with a dilution of 1+0.72. Process time 4615 mg HSA/h.

TABLE 25

Determining dilution, yield, protein sieving coefficient and process time when virus-filtering with the "dead-end" technique.

| | |
|---|---|
| Amount of protein solution after virus filtration (g): | 6380 |
| Dilution: | 1 + 0.0 |
| Yield (%): | 98 |
| Protein sieving coefficient (P/R in %): | 97–100 |
| Actual filtrate flowrate (ml/min): | 24–34 |
| Process time (mg HSA/h): | 14895 |
| Protein load ($A_{280}$ units/ft$^2$): | 124807 |
| Filtering efficiency (l/m$^2$ filter*h): | 34 |

Virus filtration of HSA when applying the "dead-end" technique means less dilution, and results in a higher yield and higher protein permeability and shorter process times.

EXAMPLE 20

Experiments were carried out with gammaglobulin as the macromolecule in a solution of high salt content, to show the effect of this type of virus-filtering technique on dilution, yield, protein sieving coefficient and process time with remaining experimental conditions being essentially constant. The gammaglobulin solution used was similar to the solution used in Example 8. The buffer contained 1.0 M NaCl+20 mM sodium acetate+0.075 M glycine (pH=5.5) in all experiments. The conditions applied were the same as those applied in Example 1, with the exception of the following differences:

| Virus filtration technique | Tangential | "Dead-end" |
|---|---|---|
| Amount of protein solution prior to virus filtration (g): | 301 | 400 |
| Protein conc. ($A_{280}$ units): | 5.1 | 4.9 |
| Retention flowrate (l/h): | 40 | 0 |
| Filtrate flowrate buffer (ml/min): | 24 | 28 |
| Transmembrane pressure (bar): | 0.2 | 0.1 |

TABLE 26

Determining dilution, yield, protein sieving coefficient and process time when using "dead-end" filtration:

| Amount of filtrate, g | P/R, % | Flowrate, ml/min |
|---|---|---|
| 50 | 92 | 17 |
| 100 | 92 | 12 |
| 150 | 93 | 9 |
| 200 | 92 | 8 |
| 250 | 90 | 7 |
| 300 | 88 | 6 |
| 350 | 87 | 5 |

| Sample | Amount, g | Protein conc., units | Yield,% |
|---|---|---|---|
| Prior to virus filtration | 400 | 4.9 | 100 |
| Filtrate | 350 | 4.6 | 82 |
| Wash | 100 | 2.3 | 12 |

A total yield of 94% was obtained over the virus filter, with a dilution degree of 1+0.12. Process time 2790 mg gammaglobulin/h.

TABLE 27

Determining dilution, yield, protein sieving coefficient and process time when using tangential virus filtration.

| | |
|---|---|
| Amount of protein solution after virus filtration (g): | 643 |
| Dilution: | 1 + 1.16 |
| Yield (%): | 92 |
| Protein sieving coefficient (P/R in %): | 43–67 |
| Actual filtrate flowrate (ml/min): | 16–20 |
| Process time (mg gamma-globulin/h): | 1873 |
| Protein load ($A_{280}$ units/ft$^2$): | 3192 |
| Filtering efficiency (l/m$^2$ filter*h): | 23 |

Virus-filtration of gammaglobulin with the "dead-end" technique involves less dilution, and results in a higher yield and protein permeability and shorter process times.

EXAMPLE 21

Experiments were carried out with antithrombin as the macromolecule, to illustrate that the present invention is applicable on an industrial scale by using a substatially bigger filter area (10 ft$^2$) than in the previous Examples (⅓ ft$^2$). A commercial solution containing antithrombin (AT III), ATenativ®, was supplied by Pharmacia AB, Stockholm, Sweden.

Experimental conditions:

Buffer: 1 M NaCl+1 mM sodium phosphate.

Total salt content: about 1.0 M.

Protein concentration: 9.2 $A_{280}$ units.

Protein solution pH: 7.4.

Amount of protein solution prior to virus filtration: 20.8 kg

Virus separating filters: Viresolve™/70.

Filtering technique: dead-end.

Filter area: 10 ft$^2$

Retention flowrate: 0 l/h.

Filtrate flowrate buffer: 20 l/h
Transmembrane pressure: 0.3 bar.

TABLE 28

Determining dilution, yield, protein sieving coefficent and process time when using a filter area of 10 ft² and dead-end filtering technique according to the invention.

| | |
|---|---|
| Amount of protein solution after virus filtration (kg): | 24.1 |
| Dilution: | 1 + 0.16 |
| Yield (%): | 96 |
| Protein sieving coefficient (P/R in %): | 94–97 |
| Actual filtrate flowrate (ml/min): | 7–12 |
| Process time (kIU AT III/h): | 735 |
| Protein load ($A_{280}$ units/ft²): | 19,136 |
| Filtration efficiency (1/m² filter*h): | 8.8 |

It is evident from this Example, that virus filtering antithrombin according to the invention can be applied on an industrial scale with excellent results.

EXAMPLE 22

The virus-removing effect achieved with the experiments disclosed in Example 15 was determined by a virus study, but at a higher salt content. The virus-filtering technique was the "dead-end" technique. The study was carried out on parvovirus, as in Example 3. The parvovirus was added to the solutions containing factor IX 1.0 M NaCl+0.01 M sodium citrate (experiment 1). The solutions were analyzed with respect to the parvovirus both before and after virus filtration.

| Experiment | Virus reduction |
|---|---|
| 1 | $1 \times 10^{5.5}$ |

The results show that virus filtration in accordance with Example 15 using dead-end technique fulfil the requirements placed by the authorities on the virus reduction in one process step. Furthermore, the use of a high salt content in accordance with the invention is at least equally as effective in removing virus as previously known techniques.

What is claimed is:

1. A filtration method for removing at least one virus selected from the group consisting of hepatitis virus A, polio virus and parvo virus from a solution containing at least one macromolecule, comprising virus-filtering the solution containing at least one macromolecule, wherein the total salt content of the solution is within the range of from about 0.2 M to 2 M.

2. A method according to claim 1, wherein the salt is selected from the group consisting of sodium chloride, potassium chloride, sodium acetate, sodium citrate, sodium phosphate, potassium dihydrophosphate and combinations thereof.

3. A method according to claim 2, wherein the macromolecule is selected form the group consisting of proteins, polycharides and polypeptides and combinations thereof.

4. A method according to claim 1, wherein the macromolecule is selected from the group consisting of proteins, polysaccharides and polypeptides and combinations thereof.

5. A method according to claim 4, wherein the macromolecule is factor IX.

6. A method according to claim 4, wherein the macromolecule is gammaglobulin.

7. A method according to claim 4, wherein the macromolecule is albumin.

8. A method according to claim 6, wherein the macromolecule is antithrombin III.

9. A method according to claim 4, wherein the macromolecule is a deletion derivative of recombinant factor VIII.

10. A method according to claim 1, wherein the virus-filtering step reduces the content of non-enveloped viruses by at least 4 logs.

11. A filtration method according to claim 1, wherein the total salt content of the solution is within the range of from about 0.2 M to 1.5 M.

12. A filtration method for removing at least one virus selected from the group consisting of hepatitis virus A, polio virus and parvo virus from a solution containing at least one macromolecule, comprising virus-filtering the solution containing at least one macromolecule, wherein the total salt content of the solution is within the range of from about 0.2 M up to saturation with the salt, and wherein the salt is selected from the group consisting of sodium chloride, potassium chloride, sodium acetate, sodium citrate, sodium phosphate, potassium dihydrophosphate and combinations thereof.

13. A method according to claim 12, wherein the total salt content of the solution is within the range of from 0.4 M to 2.0 M.

14. A method according to claim 12, wherein the macromolecule is selected from the group consisting of proteins, polysaccharides and polypeptides and combinations thereof.

15. A method according to claim 14, wherein the macromolecule is factor IX.

16. A method according to claim 14, wherein the macromolecule is gammaglobulin.

17. A method according to claim 14, wherein the macromolecule is albumin.

18. A method according to claim 14, wherein the macromolecule is antithrombin III.

19. A method according to claim 14, wherein the macromolecule is a deletion derivative of recombinant factor VIII.

20. A filtration method according to claim 12, wherein the total salt content of the solution is within the range of from about 0.2 M to 1.5 M.

21. A filtration method for removing at least one virus selected from the group consisting of hepatitis virus A, polio virus and parvo virus from a solution containing at least one macromolecule, comprising virus-filtering the solution containing at least one macromolecule, wherein the total salt content of the solution is within the range of from about 0.2 M up to saturation with the salt, and wherein the macromolecule is in solution during the virus filtering.

22. A method according to claim 21, wherein the total salt content of the solution is within the range of from 0.6 to 2.0 M.

23. A method according to claim 21, wherein the virus-filtering step comprises dead-end filtration.

24. A method according to claim 21, wherein the macromolecule is selected from the group consisting of proteins, polysaccharides and polypeptides and combinations thereof.

25. A method according to claim 24, herein the macromolecule is factor IX.

26. A method according to claim 24, wherein the macromolecule is gammaglobulin.

27. A method according to claim 24, wherein the macromolecule is albumin.

28. A method according to claim 24, wherein the macromolecule is antithrombin III.

29. A method according to claim 24, wherein the macromolecule is a deletion derivative of recombinant factor VIII.

30. A filtration method according to claim 21, wherein the total salt content of the solution is within the range of from about 0.2 M to 1.5 M.

31. A method for obtaining parvo virus, comprising filtering a solution containing the virus, at least one macromolecule, and a salt, wherein the total salt content of the solution is within the range of from about 0.2 M up to saturation of the solution with the salt and the macromolecule is in solution during the filtering step.

32. A method for obtaining polio virus for use in a vaccine, comprising filtering a solution containing the virus, at least one macromolecule, and a salt, wherein the total salt content of the solution is within the range of from about 0.2 M up to saturation of the solution with the salt and the macromolecule is in solution during the filtering step.

33. A filtration method comprising virus-filtering a solution containing at least one macromolecule, wherein the total salt content of the solution is within the range of from about 0.2 M to 2 M and the virus-filtering step employs dead-end filtration.

34. A filtration method, comprising virus-filtering a solution containing at least one macromolecule, wherein the total salt content of the solution is within the range of from about 0.6 M to 2 M.

35. A filtration method for virus-filtering a solution containing at least one macromolecule selected from the group consisting of factor VIII, factor IX, antithrombin III, human serum albumin, gammaglobulin, streptokinase, apolipoproteins, and growth hormones, comprising virus-filtering the solution containing at least one macromolecule, wherein the total salt content of the solution is within the range of from about 0.2 M to 2 M.

36. A method according to claim 35, wherein non-lipid enveloped virus is removed from the solution.

37. A method according to claim 36, wherein non-lipid enveloped virus is selected form the consisting of hepatitis virus A, polio virus and parvo virus.

38. A method according to claim 35, wherein a lipid enveloped virus is removed from the solution.

39. A method according to claim 38, wherein the lipid-enveloped virus is selected from the group consisting of hepatitis virus B, hepatitis virus C and the human immunodeficiency virus (HIV).

40. A method according to claim 35, wherein a virus smaller than about 350 nm is removed from the solution.

41. A method according to claim 40, wherein the virus removed from the solution is smaller than 200 nm.

42. A method according to claim 41, wherein the virus removed from the solution is smaller than 150 nm and larger than about 20 nm.

43. A filtration method for virus-filtering a solution containing at least one macromolecule selected from the group consisting of factor VIII, factor IX, antithrombin III, human serum albumin, gammaglobulin, streptokinase, apolipoproteins, and growth hormones, comprising virus-filtering the solution containing at least one macromolecule, wherein the total salt content of the solution is within the range of from about 0.2 M up to saturation with the salt, and wherein the salt is selected from the group consisting of sodium chloride, potassium chloride, sodium acetate, sodium citrate, sodium phosphate, potassium dihydrophosphate and combinations thereof.

44. A method according to claim 43, wherein non-lipid enveloped virus is removed from the solution.

45. A method according to claim 44, wherein the non-lipid enveloped virus is selected from the group consisting of hepatitis virus A, polio virus and parvo virus.

46. A method according to claim 43, wherein a lipid-enveloped virus is removed from the solution.

47. A method according to claim 46, wherein the lipid-enveloped virus is selected from the group consisting of hepatitis virus B, hepatitis virus C and the human immunodeficiency virus (HIV).

48. A method according to claim 43, wherein a virus smaller than about 350 nm is removed from the solution.

49. A method according to claim 48, wherein the virus removed from the solution is smaller than 200 nm.

50. A method according to claim 49, wherein the virus removed from the solution is smaller than 150 nm and larger than about 20 nm.

51. A filtration method for virus-filtering a solution containing at least one macromolecule selected from the group consisting of factor VIII, factor IX, antithrombin III, human serum albumin, gammaglobulin, streptokinase, apolipoproteins, and growth hormones, comprising virus-filtering the solution containing at least one macromolecule, wherein the total salt content of the solution is within the range of from about 0.2 M up to saturation with the salt, and wherein the macromolecule is in solution during the virus filtering.

52. A method according to claim 51, wherein non-lipid enveloped virus is removed from the solution.

53. A method according to claim 52, wherein the non-lipid enveloped virus is selected from the group consisting of hepatitis virus A, polio virus and parvo virus.

54. A method according to claim 51, wherein a lipid-enveloped virus is removed from the solution.

55. A method according to claim 54, wherein the lipid-enveloped virus is selected from the group consisting of hepatitis virus B, hepatitis virus C and the human immunodeficiency virus (HIV).

56. A method according to claim 51, wherein a virus smaller than about 350 nm is removed from the solution.

57. A method according to claim 56, wherein the virus removed from the solution is smaller than 200 nm.

58. A method according to claim 57, wherein the virus removed from the solution is smaller than 150 nm and larger than about 20 nm.

* * * * *